United States Patent
Singh et al.

(10) Patent No.: US 6,541,624 B1
(45) Date of Patent: Apr. 1, 2003

(54) **SPECIES SPECIFIC GENOMIC DNA SEQUENCES FOR IDENTIFICATION OF *ANACARDIUM OCCIDENTALE* AND THE METHOD FOR ITS UTILIZATION IN DETECTION OF CASHEW HUSK IN MADE TEA SAMPLES**

(75) Inventors: Mahipal Singh, Palampur (IN); Bandana Dhiman, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 3 days.

(21) Appl. No.: 09/698,154

(22) Filed: Oct. 30, 2000

(51) Int. Cl.[7] .............................................. C07H 21/04
(52) U.S. Cl. .................... 536/24.3; 536/23.1; 536/24.1; 435/6
(58) Field of Search .............................. 536/24.3, 23.1, 536/24.1; 435/6

(56) References Cited

PUBLICATIONS

Silva et al. Acta Horticulturae, Sep. 1995, No. 370. pp. 20–26.*
*The Assam Review and Tea News* 87:28–29 (Jan. 1999).
Divya Himachal (Jul. 23, 1999).
Garg, Sunita in *Substitute and Adulterant Plants* (Periodical Experts Book Agency, New Delhi, India, 1992), pp. 136–142.
Martsinkovskaya et al., "Potential Use of PCR–Amplified Ribosomal Intergenic Sequences for Differentiation of Varieties and Species of Gossyplum Cotton," *Plant Molecular Biology Reporter* 14(1):44–49 (1996).
Sudershan et al., "Changing Profile of Food Adulteration: Perception of Food Analysis," *J. Food Sci. Technol.* 32(5):368–372 (1995).
Singh et al., "Isolation and PCR Amplification of Genomic DNA From Market Samples of Dry Tea", *Plant Molecular Biology Reporter*, vol. 17:171–178, (1999).

* cited by examiner

*Primary Examiner*—W. Gary Jones
*Assistant Examiner*—Juliet C. Einsmann
(74) *Attorney, Agent, or Firm*—Foley & Lardner

(57) ABSTRACT

This invention relates to Anacardium sp. specific genomic DNA sequence and the methods for utilization of these sequences in detection of Cashew husk in tea samples. Particularly this invention relates to a very sensitive, accurate and efficient method of identification of *Anacardium occidentale* (cashew) species. The method is designed to detect presence of any part of cashew plant including the dried and ground apple in market samples of made tea. The main application of this invention is to detect the adulteration of loose as well as branded tea by any part of cashew plant and thus is a part of quality control measures, in addition to the taxonomical authentication of cashew plants.

4 Claims, 3 Drawing Sheets

Figure 1:
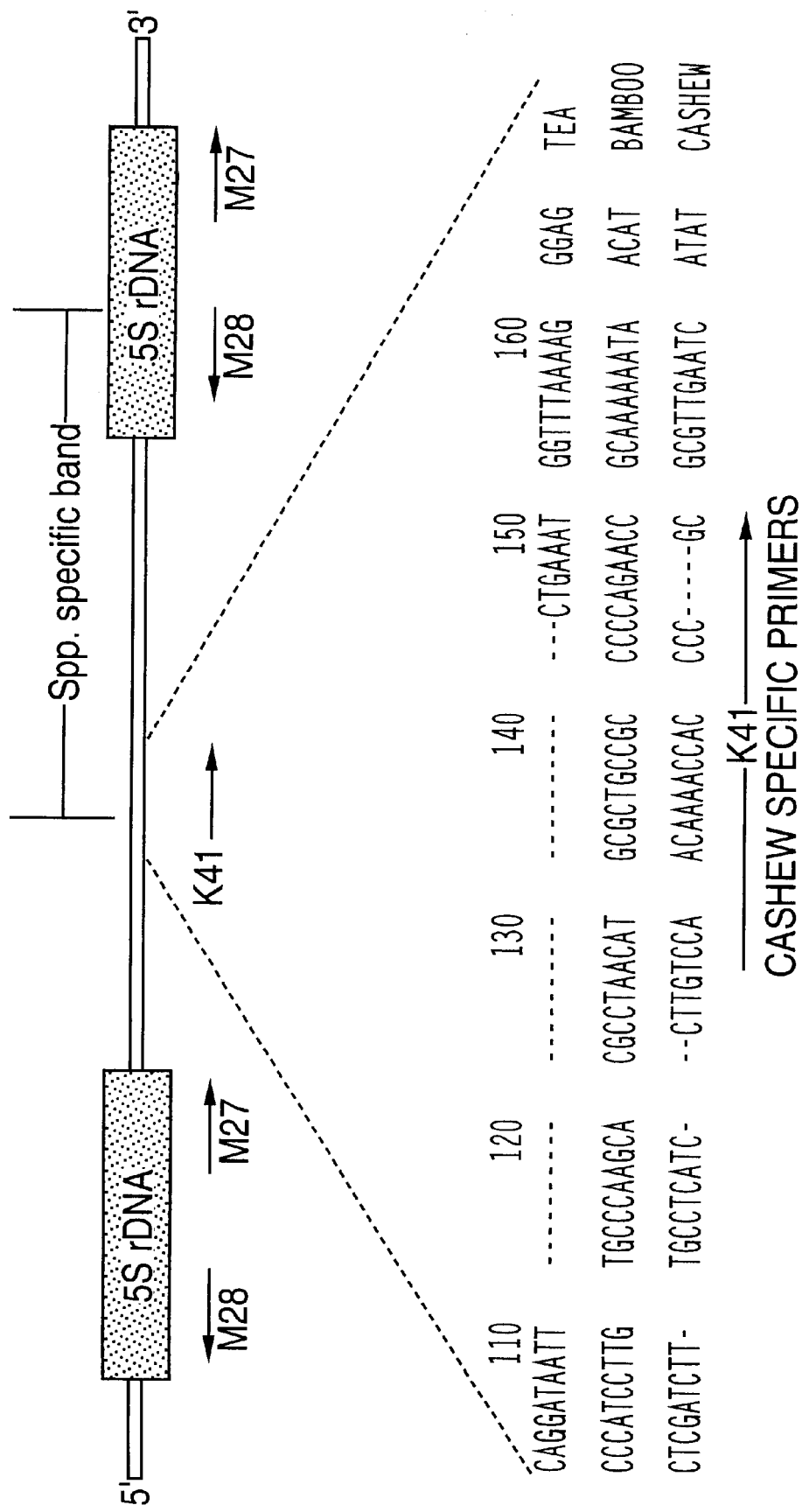

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
tttagtgctg gtatgatcgc                                               20
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
tgggaagtcc tcgtgttgca                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tgggaagtcc tcgtgttgca                                                    20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
cgccagggtt ttcccagtca cgac                                               24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 5
tcatccttgt ccaacaaaac caccccgc                                           28

<210> SEQ ID NO 6
<211> LENGTH: 31
<212> TYPE: DNA
<213> ORGANISM: Camellia sinensis

<400> SEQUENCE: 6
caggataatt ctgaaatggt ttaaaaggga g                                       31

<210> SEQ ID NO 7
<211> LENGTH: 64
<212> TYPE: DNA
<213> ORGANISM: Dendrocalamus hamiltonii

<400> SEQUENCE: 7
cccatccttg tgcccaagca cgcctaacat gcgctgcggc cccagaaacc gcaaaaaata        60
acat                                                                     64

<210> SEQ ID NO 8
<211> LENGTH: 55
<212> TYPE: DNA
<213> ORGANISM: Anacardium occidentale

```
<400> SEQUENCE: 8
ctcgatcttt gcctcatcct tgtccaacaa aaccacccg cgggttgaat catat        55
```

SPECIES SPECIFIC GENOMIC DNA SEQUENCES FOR IDENTIFICATION OF *ANACARDIUM OCCIDENTALE* AND THE METHOD FOR ITS UTILIZATION IN DETECTION OF CASHEW HUSK IN MADE TEA SAMPLES

FIELD OF THE INVENTION

The present invention provides Anacardium sp. specific genomic DNA sequence and the methods for utilization of these sequences in detection of Cashew husk in tea samples. Particularly this invention relates to a very sensitive, accurate and efficient method of identification of *Anacardium occidentale* (cashew) species. More particularly, the method is designed to detect presence of any part of cashew plant including the dried and ground apple in market samples of made tea.

The main application of this invention is to detect the adulteration of loose as well as branded tea by any part of cashew plant (and thus can be part of quality control measures) in addition to the taxonomical authentication of cashew plants.

BACKGROUND AND PRIOR ART OF THE INVENTION

Tea is a non-alcoholic beverage with consumption through out the world. It is produced by processing youngest two leaves and a bud of a plant [*Camellia sinensis* (Linn). O Kuntze] of family Theaceae (Wight, W., 1959, *Nature*, 8317: 26–28; Banerjee, B., 1988, *Nature* (London), 332: 580). It is mainly produced in India, China, Srilanka, Kenya and Japan (Singh, I. D., 1979, *Two & A Bud*, 26: 23–26), rest of the world procures tea from these producing countries. There is an increasing trend of consumer market for tea in India and abroad. Although tea production has increased world wide, for example, in India it has increased from 320 million Kg in 1960 to 870 million kg in 1988 (Anonymous, 1999-I, *Contemporary Tea Time*, 8(3): 31), there seems to be limit to meet the world demand. Tea is a health drink and is popular due to its stimulatory properties. It is also a physiological function modulating drink and is reported to act against a number of abnormalities including artherosclerosis, radiation damage, antioxidative, anticancer, antiulceric, antiviral, germicidal etc (Chen, Z., 1999, In "Global Advances in Tea Science" edited by N K Jain, Publishers: Aravali Books International (P) Ltd., New Delhi. pp333–358). It has been reported that sometimes leaves, husks, barks and other parts of some plants are used as substitute and/or adulterants of tea, for example *Acacia arabica* (Babul or kikar) bark after being used in tanning hide is converted into a powder resembling tea and is sold as such in market (Israel, A. H. & Issar, R. K., 1973, *Indian J Pharmacy*, 35: 208–209). In a survey conducted by Sudershan & Bhat (Sudershan, R. V. & Bhat, R. V., 1995, *J. Food Sci. Technol.*, 32(5): 368–372), 8 adulterants of tea namely cashew husk, iron fillings, colour, blackgram husk, other foreign leaves, exhausted tea leaves & saw dust were reported in 9% of the samples collected from various state food laboratories of India. *Acer negundo, Adiantium cappillus veneris, Albizia amara, Chenopodium ambrosioides, Epilobium angustifolium* and *Fragaria vesca* leaves have also been reported to be used in some tea either as substitute or adulterants (Garg, S., 1992, In *Substitute and Adulterant Plants*, Ist Edn. pp. 136–142, Published at "Periodical Experts Book Agency", New Delhi). Powdered animal hide has also been reported to be mixed with dry tea and sold in open market on cheaper rates (Anonymous, 1999-II, *Divya Himalchal*, 22 July). In another survey of 25 loose tea samples collected randomly from different parts of India, 80% were found adulterated with foreign vegetables, saw dust, sand, stones, stalk and used tea leaves (Anonymous, 1999-III, *The Assam Review and Tea News*, 87: 28–29). Adulteration leads to health risks to the society, since many of these adulterants are carcinogenic and many adulterant plants have side effects. Although intense surveys needs to be done not only on loose tea available in the market but also on branded tea, there is sufficient evidence about the adulteration of made tea. There is an intense need to identify adulterants in tea, which is not possible, many a times by visual inspection or by measuring only ash values. There are currently no methods available to identify the adulteration of tea for many of the above said adulterants. Use of molecular tools in such cases could be ideal, specially, when most of the adulterants are biological substances. During processing the tea, degrades much of the cells and their DNA, and only the degraded DNA can be isolated (Singh, M., Bandana & Ahuja, P. S., 1999, *Plant Mol. Biol. Reporter*, 17 & 171–78), it can be suitable only for PCR based techniques. Recently conserved sequences including 5S rRNA genes and their spacer length variability has been utilized to differentiate fungal species (Moukhamedov, R. S., Hu, X., Nazar, R. N. & Robb, J., 1994, *Phytopathology*, 83: 256–259), to identify the plant varieties (Martsinkovskaya, A. I., Moukhamedov, R. S., & Abdukarimov, A. A., 1996, *Plant Mol. Biol. Reporter*, 14: 44–49) and to detect cereal composition in admixtures (Ko, H. L. & Henry, R. J., 1996, Plant Mol. Biol. Reporter, 14 (1): 33:43). Using the same approach, we have cloned and sequenced the spacer regions between 5S rRNA genes in 3 plants species and have developed a protocol to utilise the sequence differences to detect the adulteration of cashew husk in dry market tea samples by Polymerase Chain Reaction.

OBJECTS OF THE INVENTION

The main objective of the present invention is to provide a species-specific DNA sequence and its utilization in detection of *Anacardium occidentale*.

Another object of this invention is to provide a PCR based method to detect adulteration of tea by cashew husk or any other part of cashew plant.

DETAILED DESCRIPTION OF THE INVENTION

The present invention provides Anacardium sp. specific genomic DNA sequence and the methods for utilization of these sequences in detection of Cashew husk in tea samples. This invention relates to a very sensitive, accurate and efficient method of identification of *Anacardium occidentale* (cashew) species. Particularly, the method is designed to detect presence of any part of cashew plant including the dried and ground apple in market samples of made tea.

The main application of this invention is to detect the adulteration of loose as well as branded tea by any part of cashew plant (and thus is a part of quality control measures) in addition to the taxonomical authentication of cashew plants.

BRIEF DESCRIPTION OF THE ACCOMPANYING DRAWINGS

The invention is illustrated by the accompanying drawings wherein:

FIG. 1 shows Sequence comparison (SEQ ID NOS 6–8, respectively, in order of appearance) of 5S rRNA gene (s) and their spacer regions:

Sequence comparison of the parts of spacer region between 5S rRNA genes is shown in three different plant species. M 27 and M 28 forward and reverse consensus 5S rRNA primers respectively. K41 is a specific primer based on the DNA sequence of *Anacardium occidentale* (cashew). The expected amplification product using one consensus (M28) and the other cashew specific (K41) primers is shown above the 5S rRNA genes.

Figure 2:
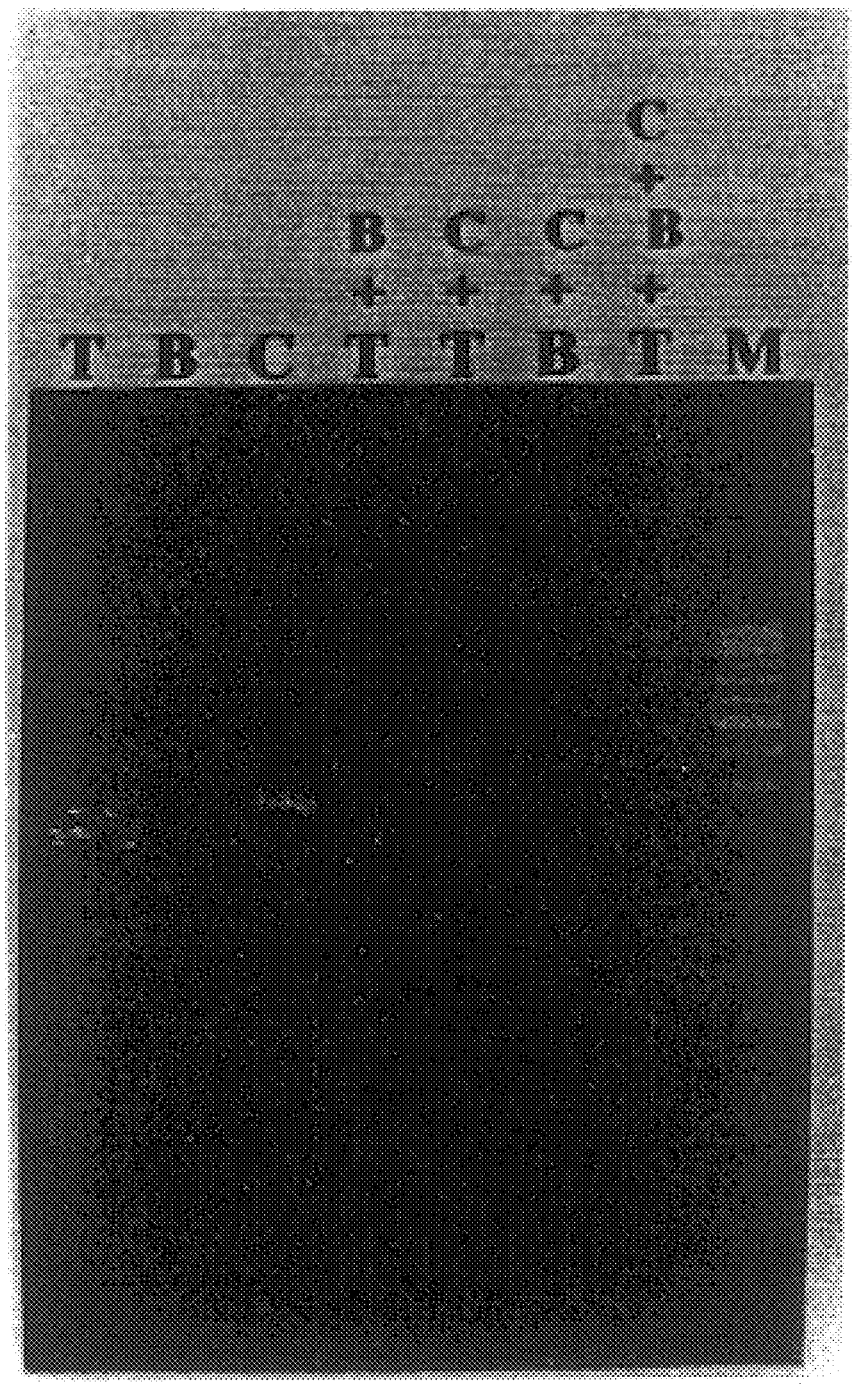

FIG. 2 shows PCR amplified products using one of the conserved 5S rRNA primer and the other cashew specific primers:

Lanes T, B and C are *Camellia sinesis, Dendrocalamus hamiltonii* and *Anacardium occidentale* respectively. Rests of the lanes have 1:1 mixture of the corresponding plant genomic DNAs. M is mol. wt. marker 100 bp ladder. Primer sets used were M28 & K41.

Figure 3:
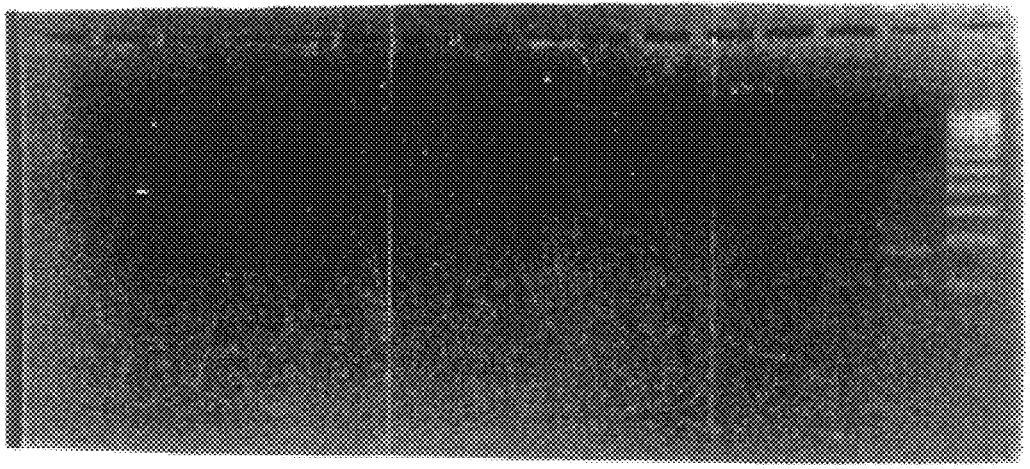

FIG. 3 shows PCR products of 12 different tea cultivars using primers M28 and K41:

Lanes 1 to 12 are different tea cultivars as shown in Table 1. C is cashew. M is mol wt marker 100 bp ladder.

Figure 4:
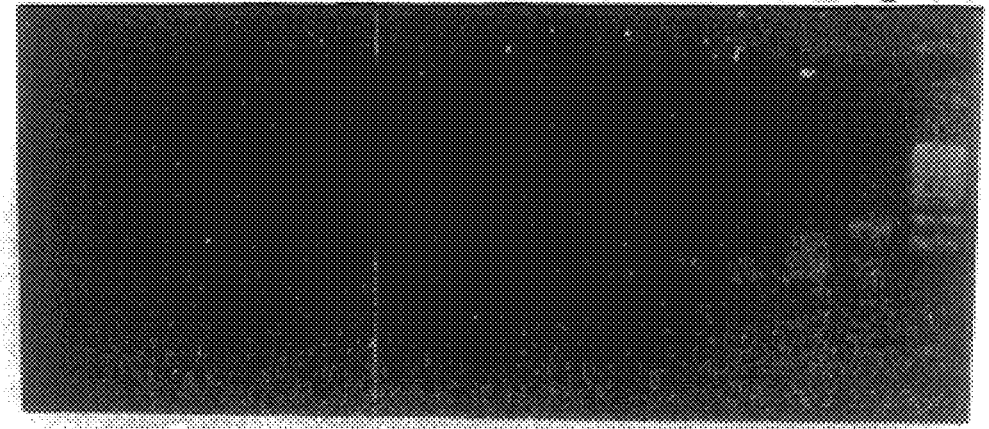

FIG. 4 shows PCR products of 9 different plant species, human, animal and *E. Coli* genomes:

Lanes 1 to 9 are different plant species eg. *Nicotiana tabaccum, Artemisia vulgaris*, Philodendron, *Valeriana jatamamshi, Rosa damascena, Ocimum sanctum*, Oleracea spp., *Mentha piperata* and *Phaseolus vulgaris* respectively. Lane H, A and E are human, animal and bacterial DNA respectively. C is cashew, B is blank without template DNA and M is mol wt marker 100 bp ladder. The primer set used here was M28K41.

Accordingly, the present invention provides species specific genome DNA sequence for identification of *Anacardium occidentale* and the method of its utilization in detection of cashew husk in made tea samples which comprises:

a) a unique sequence of cashew DNA which is absent in tea genome, b) a unique set of cashew specific PCR primers, c) a PCR based method to identify *Anacardium occidentale* species and d) a PCR based method to detect adulteration of cashew husk in made or processed tea.

In an embodiment of the present invention genomic DNA from 12 different commercial tea cultivars are used (table 1)

TABLE 1

List of the various commercial tea cultivars used in this study.

| Sl. No. | Name of the genotype |
|---|---|
| 1. | TRA/HV39 |
| 2. | EC |
| 3. | Kangra-Jat |
| 4. | UPASI-10 |
| 5. | CSIN-303536 |
| 6. | TV-23 |
| 7. | TV-4 |
| 8. | UPASI-3 |
| 9. | UPASI-13 |
| 10. | ST-449 |
| 11. | TV-1 |
| 12. | CIAP-303535 |

In another embodiment of the present invention genomic DNA from nine different plant species are used (table 2).

TABLE 2

List of the various plant species used in this study

| Sl. No. | Species Name |
|---|---|
| 1. | *Nicotiana tabaccum* |
| 2. | *Artemisia vulgaris* |
| 3. | Philodendron spp. |
| 4. | *Valeriana jatamamshi* |
| 5. | *Rosa damascena* |
| 6. | *Ocimum sanctum* |
| 7. | Oleracea spp. |
| 8. | *Mentha piperata* |
| 9. | *Phaseolus vulgaris* |

In yet another embodiment of the present invention genomic DNA from cashew husk and various made tea samples are used.

In yet another embodiment of the present invention, plasma pMOS Blue-T vector DNA is used.

PCR Amplification, Cloning and Sequencing of the Amplified Products

The consensus primers complementary to and based on the sequences of the 3' and 5' ends of the 5S rRNA gene coding regions for plants as described earlier (Cox, A. V., Bennett, M. D., & Dyer, T. A., 1992, *Theor Apl Genet*, 83: 684–90; Kanazin V., Ananiev, E. & Blake, T., 1993 Genome, 36: 1023–1028) are synthesized by "Bangalore Genei (pvt) Ltd", India. The sequences of these forward and reverse primers are (SEQ ID NO: 1) 5'-TTTAGTGCTGGTATGATCGC-3' (M27) AND (SEQ ID NO: 2) 5'-TGGGAAGTCCTCGTGTTGCA-3' (M28) respectively. They are used to amplify the non-coding spacer regions between 5S rRNA genes. The PCR is performed in a Robocycler from Stratagene. The machine is programmed for 1 cycle at 94° C. for 3' and then for 40 cycles at 94° C., 30 sec; 68° C. 30 sec and 72° C. 30 sec. The final extension cycle at 72° C. was kept for 7 minutes. The PCR product is then analyzed in a 1.4% agarose gel to obtain 2–7 bands in the range of 250 bps to 1.4 kb in tea, bamboo and cashew. The intensity of the bands is found different and usually the lowest band is most intense. A maximum of 7 bands in tea, while in cashew and bamboo only 3 bands in each are obtained. The lowest densely visible bands in all the three species are excised from the agarose gels and purifying the gels using QIA quick gel extraction kit from Qiagen. Ligating the purified DNA with pMOS Blue-T vector overnight at 16° C. as per manufacturer's instructions (Amersham Life Sciences), transforming the mixture into *E. Coli* MOS Blue cells, selecting onto X-Gal, IPTG and ampicillin (50 µg/ml) plates, analyzing ten white colonies in each case for right insert (Sambrook, J., Fritisch, E. F. & Maniatis, T., 1989, Molecular Cloning: A laboratory manual, 2nd Edn., Cold Spring Harbour Laboratory Press, N.Y.) and finally sequencing one plasmid clone from each plant in both the directions using the T7 promotor primer (SEQ ID NO: 3) (5'-TAATACGACTCACTATAGGG-3') and M13 forward primer (SEQ ID NO: 4) (5'-CGCCAGGGTTTTCCCAGTCACGAC-3') on an Applied Biosystems model 377 automatic DNA sequencing system.

In an embodiment of the present invention, K-41 and M-28 are the primers providing a single band as PCR product of 160 bps in *Anacardium occidentale*.

In another embodiment the sequences is specific at an optimized PCR cycling temperatures (denaturation at 94° C., annealing at 62° C. and extension at 72° C.).

In still another embodiment the sequences is specific at an optimized PCR cycling times (denaturation for 30 seconds, annealing 25 seconds and extension for 17 seconds).

In yet another embodiment the sequences is specific at an optimized MgCl₂ ion concentration of 1.05 mM.

Sequence Analysis and Species Specific Primer Design

The sequencing data obtained from spacer regions between 5SrRNA genes are analyzed using the PC Gene software from "Oxford Biomolecular Group". Sequence analysis reveals that cloned spacer fragments are 199, 224 and 299 bps long for tea, bamboo and cashew respectively. Sequence comparisons using CLUSTAL program shows 256 bps as consensus length, of which 43 bps (16.8%) are identical and 81 (31.6%) are found similar. Sequence reveals high degree of variability in 3 species. There is a stretch of about 33 bps completely absent in tea, which is used to design cashew specific primers. The complementary sequence from spacer region [28 bps primer K41, (SEQ ID NO: 5) 5'-TCATCCTTGTCCAACAAAACCACCCCCC-3'] specific to the *Anacardium occidentale* species is found absent in tea and very dissimilar in bamboo and is selected to be used as specific nested primer (FIG. 1).

The following examples are given by way of illustration of the present invention and should not be construed to limit the scope of the present invention.

Example 1

Cashew Specific Primers Amplify Only Cashew Genomes

PCR amplification using one of the cashew specific and the other consensus 5S rRNA gene primers (as illustrated in FIG. 1) is obtained using the M28/K41 set of primers. The PCR conditions followed are as described above for the consensus 5SrRNA gene primers. The result shows that the M28/K41 set of primer gives a band of 160 bps with only cashew as expected but not with tea or bamboo plants. There is also a similar amplification product when the genomic DNA of all the three plant species is mixed in equal ratio, however, the intensity of the band is reduced. Three parameter i.e. annealing time, Mg⁺⁺ and primer concentrations are optimized. It is observed that a PCR reaction of 1 cycle at 94° C. denaturation for 3' and then 40 cycle at 94° C., 30 sec; 62° C., 25 sec and 72° C., 17 sec and then a final extension cycle of 3' at 72° C. is optimum to get the single band with sufficient intensity (FIG. 2). A 2.8 picomole concentration of primer is optimum, 100 μM of dNTPs and 1.05 mM MgCl₂ gives the maximum intense bands. The PCR product is cashew genome specific and can be detected reproducibly in mixture of all the 3 plant species. There is no significant difference in the band intensity when the genomic DNA from fresh tissues or the dried tissues i.e. processed made tea, cashew husk etc are taken. It is further observed that if the annealing time is increased beyond 25 sec, sometimes a few high molecular weight faint bands appear especially in bamboo species. Similarly, if the extension time is increased beyond 17 seconds there are few faint bands of high molecular weight.

Example 2

Cashew Specific Primers do not Amplify 12 Commercially Grown Tea Cultivar's DNA

The cashew specific primer set (M28/K41) is used to amplify genomic DNA isolated from 12 different commercial tea producing cultivars. As shown in FIG. 3, none of the cultivars genomic DNA can be amplified when clearly demonstrate that the method can be used for any brand of tea.

Example 3

Cashew Specific Primers do not Amplify Majority of the Plant Species, Human, Animal and Bacterial Genomes The cashew specific primer set (M28/K41) is also used to amplify genomic DNA from 9 different plant species and one each of human, animal and bacterial genomic DNAs. As shown in FIG. 4, none of the species can show the expected amplification product. There is a faint amplification product in Valeriana, which is smaller ( about 120 bps) in size. Similarly, a band appears in *E. Coli* but its size is much smaller(about 90 bps) as against the 160 bps specific product. In human genome also there seems to be a 50 bp small amplification product. All these smaller PCR products are distinguishable from the cashew specific PCR product.

The main advantages of the present invention are:

1) It is specific to *Anacardium occidentale*.
2) It is highly sensitive and only nanogram amounts of DNA are required.
3) It can work equally well for degraded DNA.
4) It can work well for the processed tea samples which have undergone high processing temperatures.
5) It can detect presence of any cashew tissues even in admixtures of samples.
6) The presence of cashew specific PCR product can be visualized in simple agarose gels and no hazardous radioactive labeling or time consuming and complex systems are needed.
7) It is rapid.
8) It has a potential for automation.

What is claimed is:

1. An isolated PCR product consisting of SEQ ID NO: 8, obtainable by PCR using a cashew-specific primer, wherein said isolated PCR product is specific for *A. occidentale*.

2. The isolated PCR product of claim 1, wherein said cashew-specific primer is a nucleic acid molecule consisting of the nucleotide sequence in SEQ ID NO: 5.

3. A cashew-specific primer consisting of an isolated nucleic acid molecule comprising SEQ ID NO: 5.

4. An isolated nucleic acid molecule consisting of the nucleotide sequence in SEQ ID NO. 8.

* * * * *